United States Patent [19]

Nylander

[11] Patent Number: 5,434,778
[45] Date of Patent: Jul. 18, 1995

[54] METHOD AND APPARATUS FOR MEASURING PREVAILING WEATHER AND METEOROLOGICAL VISIBILITY

[75] Inventor: Pauli Nylander, Helsinki, Finland

[73] Assignee: Vaisala Oy, Helsinki, Finland

[21] Appl. No.: 232,419

[22] Filed: Apr. 25, 1994

Related U.S. Application Data

[63] Continuation of Ser. No. 866,360, Apr. 10, 1992, abandoned.

[30] Foreign Application Priority Data

Apr. 22, 1991 [FI] Finland .................................. 911932

[51] Int. Cl.⁶ .............................................. G01V 1/00
[52] U.S. Cl. .................................. 364/420; 73/170.17; 340/580
[58] Field of Search .............................. 364/420, 421; 340/580–583, 600–601; 73/170.17, 170.16

[56] References Cited

U.S. PATENT DOCUMENTS

| | | | |
|---|---|---|---|
| 3,141,330 | 12/1960 | Murray et al. | 73/170.17 |
| 4,613,938 | 9/1986 | Hansen et al. | 364/420 |
| 4,760,272 | 7/1988 | Wang . | |
| 5,125,268 | 6/1992 | Caron | 73/170.17 |

FOREIGN PATENT DOCUMENTS

| | | |
|---|---|---|
| 61-172032 | 8/1986 | Japan . |
| 2300688 | 12/1990 | Japan . |
| 2300692 | 12/1990 | Japan . |

OTHER PUBLICATIONS

Artech House Inc., Radar and the Atmosphere, A. J. Bogunh, Jr., 1989 pp. 277–295.
Introduction to Radar Systems, Merrill Skolnik, McGraw-Hill Book Company 1962 pp. 539–547.

Primary Examiner—Gail O. Hayes
Assistant Examiner—Frantzy Poinvil
Attorney, Agent, or Firm—Birch, Stewart, Kolasch & Birch

[57] ABSTRACT

A method and apparatus measuring prevailing weather and meteorological visibility. According to the method an optical scattering-type measurement instrument is used for determining the apparent volume of precipitation in a measurement space. The apparent volume of precipitation is measured in measurement space having a volume of less than 0.2 liters, and simultaneously with this measurement of apparent volume of precipitation, also the water quantity related to the measurement space is measured. The implementation makes it possible to determine both the type and rate of precipitation.

12 Claims, 5 Drawing Sheets

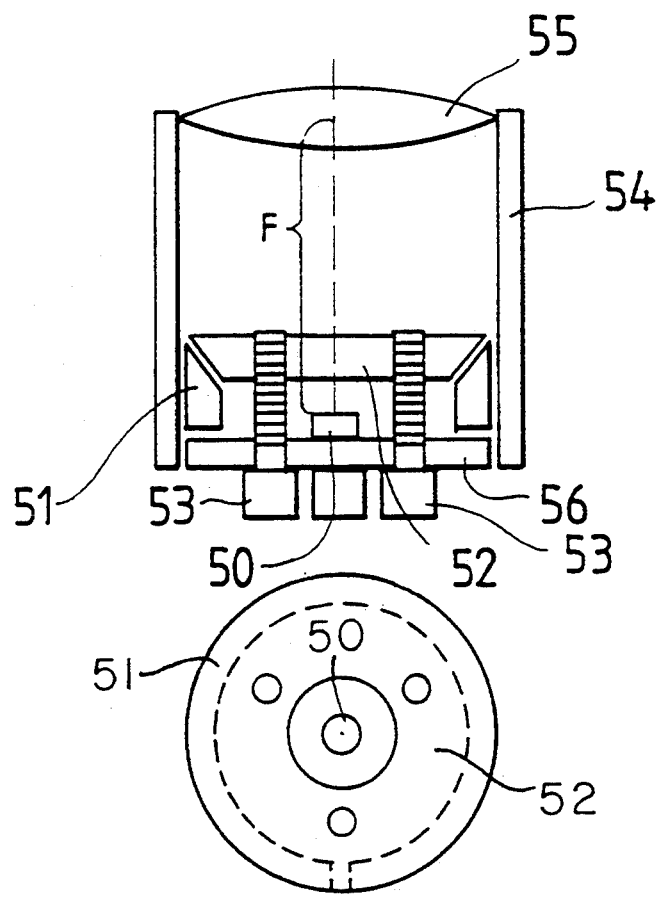

METHOD AND APPARATUS FOR MEASURING PREVAILING WEATHER AND METEOROLOGICAL VISIBILITY

This application is a continuation of application Ser. No. 07/866,360 filed on Apr. 10, 1992, now abandoned.

BACKGROUND OF THE INVENTION

Field of the Invention

The present invention relates to a method for measuring prevailing weather and meteorological visibility.

The present invention also concerns an apparatus for measuring prevailing weather and meteorological visibility.

An important part of weather observation is the determination of prevailing weather. The codes for prevailing weather in an international weather message include the possibility of reporting observations principally related to total cloudiness, air turbulence and type/rate of precipitation as well as different disturbance phenomena (e.g., lightning, storms).

The method and apparatus disclosed herein makes it possible to determine, on the basis of measurements, most of the parameters related to precipitation. This can appreciably promote the automation of weather observation, which in turn enables shorter intervals between weather observations and denser networks of observation points as well as their location to noninhabited regions, for instance. Precipitation in this context means precipitation of condensed moisture in all possible forms.

Accurate measurement of meteorological visibility in all weather conditions forms an essential part of weather information, in particular prevailing weather at airports.

Most conventional equipment detects only the advent and cessation of precipitation, or alternatively, measure the rate of precipitation. Analysis of precipitation in the scope dealt with in the present invention has not earlier been attempted in a single apparatus. Closest to this goal has been reached by apparatuses based on the analysis of the optical measurement signal and various types of microwave weather radars.

The key problem in precipitation analysis is the differentiation of liquid forms of water from its solid condensation forms such as hailstones and snowflakes from each other at all rates of precipitation and all weather conditions (wind, radiance, temperature). This is not possible with prior art apparatuses and methods.

Optical methods known in the art are of two types: A method based on scatter measurement of light transmitted by the apparatus and scintillation measurement of transmitted light. Furthermore, several different apparatuses based on light transmission measurement are known that are predominantly used for measurement of droplet diameter distributions.

An apparatus based on scatter measurement (U.S. Pat. No. 4,613,938) aims to detect particulate matter and measure the size and speed of particles in a sample volume which due to optical design constraints must be larger than 0.2 liters. Based on the analysis of particle sizes and speeds, a sorting matrix is formed in which large and slow particles are designated as snow, large and fast particles as hail, etc.

Only a statistical measurement of the particle size distribution is possible by means of the above-described apparatus, because the sample volume is relatively large and undefined, and the speed of the wind driving the particles can be of the same order of magnitude (approx. 5 m/s) as the falling particles gain by gravity fall. The impossibility of speed measurement was, in fact, later recognized by the patentee, after which he has added a second optical receiver to the apparatus. Yet, even a second optical receiver does not remove uncertainty from the particle speed measurement. Furthermore, the rain matrix entails overlapping of different rain types at low precipitation rates. Evidently, the sample volume required for the particle size distribution is excessively large, because even at relatively low rates of precipitation the sample volume contains several particles simultaneously.

An apparatus based on scintillation measurement determines the energy distribution at different frequencies for the scintillation of incident light from spherical particles (U.S. Pat. No. 4,760,272). According to measurements, the energy of light scintillation from water particles concentrates at higher frequencies that those encountered with snow. The intensity of scintillation allows the detection of precipitation advent and cessation as well as its rate. The speed of the particles affects the signal amplitude and quality, thereby restricting the decision making capability between different types of precipitation. Turbulence caused in windy conditions by the mechanical construction of the apparatus disturbs the measurement, and this drawback cannot be eliminated entirely. Furthermore, the shimmer effect caused by the heating of air is detected as a scintillation signal.

An apparatus based on a microwave radar aims to measure the rate of fall of particles with the help of the Doppler effect. Sorting of rain type is based on the differences in the rates of fall for the different types of precipitation. The large volume of sample space and wind can disturb the measurement. In wind, snowfall is detected as rainfall. Dripping rainfall easily is interpreted as snowfall, because the small droplets fall extremely slowly. Low rates of rainfall are not detected at all as precipitation.

Thus, conventional apparatuses permit a relatively reliable detection of the advent and cessation of precipitation alone.

Visibility measurement meters based on the measurement of light scattering operate relatively well in fog approaching drizzle, whereby their operation conforms to the scattering theory. In rainfall the particle size vastly exceeds the wavelength of incident light, thereby invalidating the preconditions of scattering theory. Furthermore, the optical properties and size distributions of snow and water differ from each other. Without corrections by type and rate of precipitation, the visibility reading of a scattering-type visibility meter is not reliable in all weather conditions.

SUMMARY OF THE INVENTION

It is an object of the present invention to overcome the disadvantages related to the above-described prior-art techniques and to achieve an entirely novel method and apparatus for the measurement of prevailing weather and meteorological visibility.

The method is based on the simultaneous measurement of apparent volume of precipitation and the quantity of water contained in the sample space.

More specifically, the method according to the invention measures prevailing weather and meteorological visibility, comprising the steps of optically measuring an apparent volume of precipitation in a measurement space, having a volume of less than 0.2 liters, and simultaneously measuring a water quantity related to the measurement space.

Furthermore, the apparatus according to the invention measures prevailing weather and meteorological visibility, said apparatus comprising optical scattering-type measurement means for measuring an apparent volume of precipitation in a measurement space, means for measuring water quantity related to the apparent volume of precipitation in the measurement space, and data-processing means for determining a precipitation type from the measured apparent volume and the measured water quantity.

The invention offers significant benefits.

Liquid form of water has a density of 1.0, while in solid condensation form the density of water is from 0.9 to 0.01. Typical density of snow is 0.1, whereby a 10 mm layer of snow equals to 1 mm of rain. On this basis it is evident that even a relatively inaccurate measurement of the apparent volume of precipitating particles and the quantity of contained water differentiates melted water from solid condensation forms of water. Due to the measurement method of water quantity, the method according to the invention is rather benefitted than hampered by the prevailing wind during precipitation, as only a portion of particles occurring in solid condensation form are detected. This is because a portion of the snow fails to adhere to the heated measuring surface, but rather, is carried away with the wind. This fact contributes to increased difference in the volume comparison against the measured quantity of water.

A capacitive measurement technique of water volume eliminates incorrect precipitation signals caused by possibly occurring insects, dust, sand, etc. Moreover, this technique provides extreme sensitivity in moisture measurement down to very low measured volumes of water.

The small volume of sample space in the optical measurement improves the signal-to-noise ratio, because the intensity of the emitted light on the surface of the scattering particle becomes higher than by emitting at the same optical power output into a larger volume of sample space. Additionally, the risk of having several particles in the sample space simultaneously is reduced.

A scattering-type visibility measurement system operating without correction for precipitation gives poor readings during precipitation. Now, the correction of the measurement reading on the basis of detected precipitation information is utilized.

BRIEF DESCRIPTION OF THE DRAWINGS

The invention is next examined in greater detail with the help of exemplifying embodiments illustrated in the appended drawings, in which

FIG. 5 shows diagrammatically both a side and a top view of a mounting method of a transmitter/receiver unit according to the invention.

DESCRIPTION OF THE PREFERRED EMBODIMENT

Figure 1:
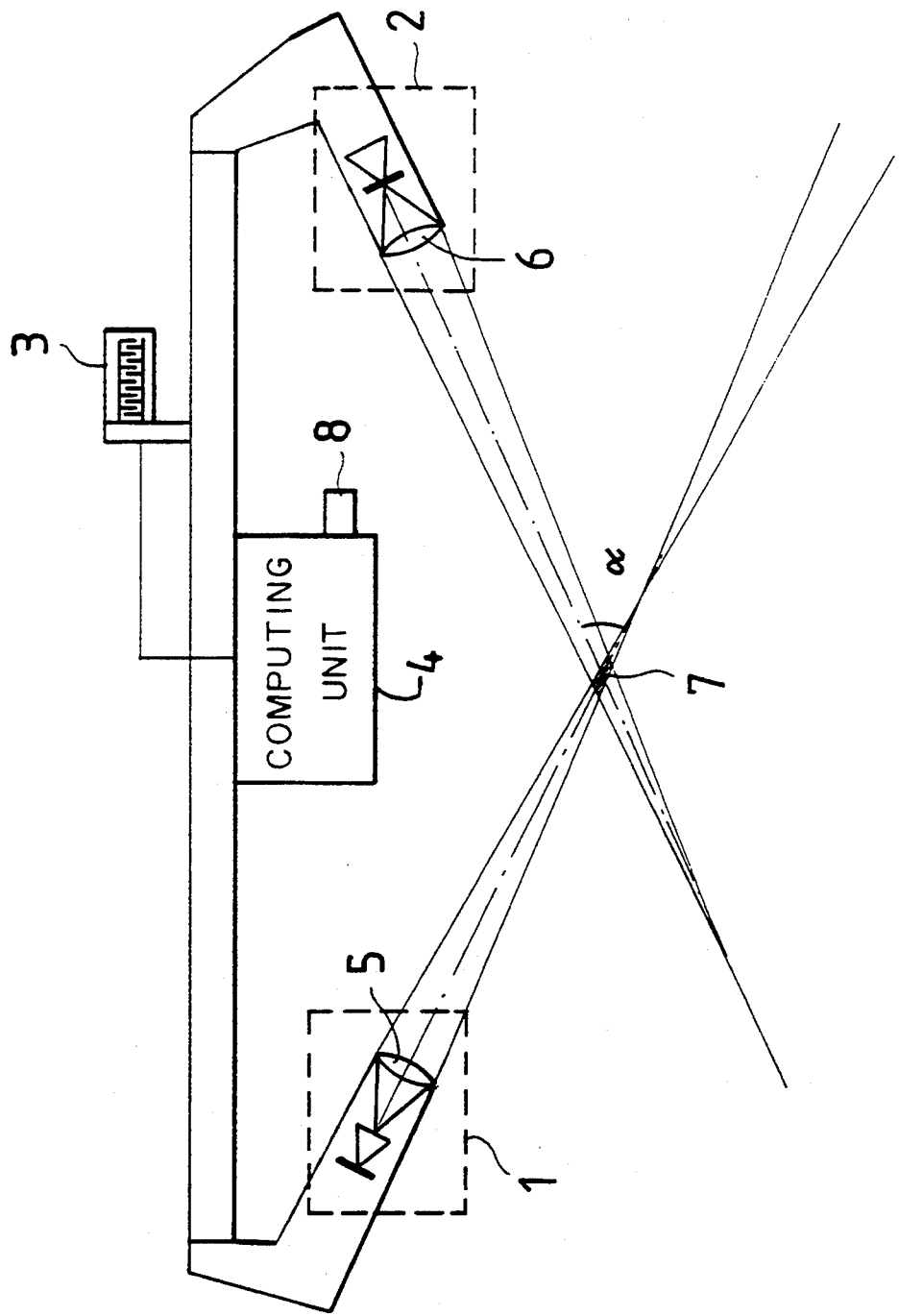
FIG. 1 shows a measurement apparatus based on narrow-angle optics according to the invention for measuring prevailing weather and visibility.

According to FIG. 1, a transmitter unit 2 and a receiver unit 1 are connected to a computing unit 4. The optical axes of the transmitter unit 2 and the receiver unit 1 make an angle $\alpha$ which advantageously is 33°. The beams formed by a lens 6 of the transmitter unit 2 and a lens 5 of the receiver unit 1 intersect, thereby delineating at their intersection point a measurement space 7 having advantageously a volume less than 0.2 l. The measurement of water volume is implemented with the help of a heatable capacitive sensor 3, which is connected to the computing unit 4. The temperature prevailing in the measurement space 7 is further measured with the help of a sensor 8, which also is connected to the computing unit 4.

Figure 2:
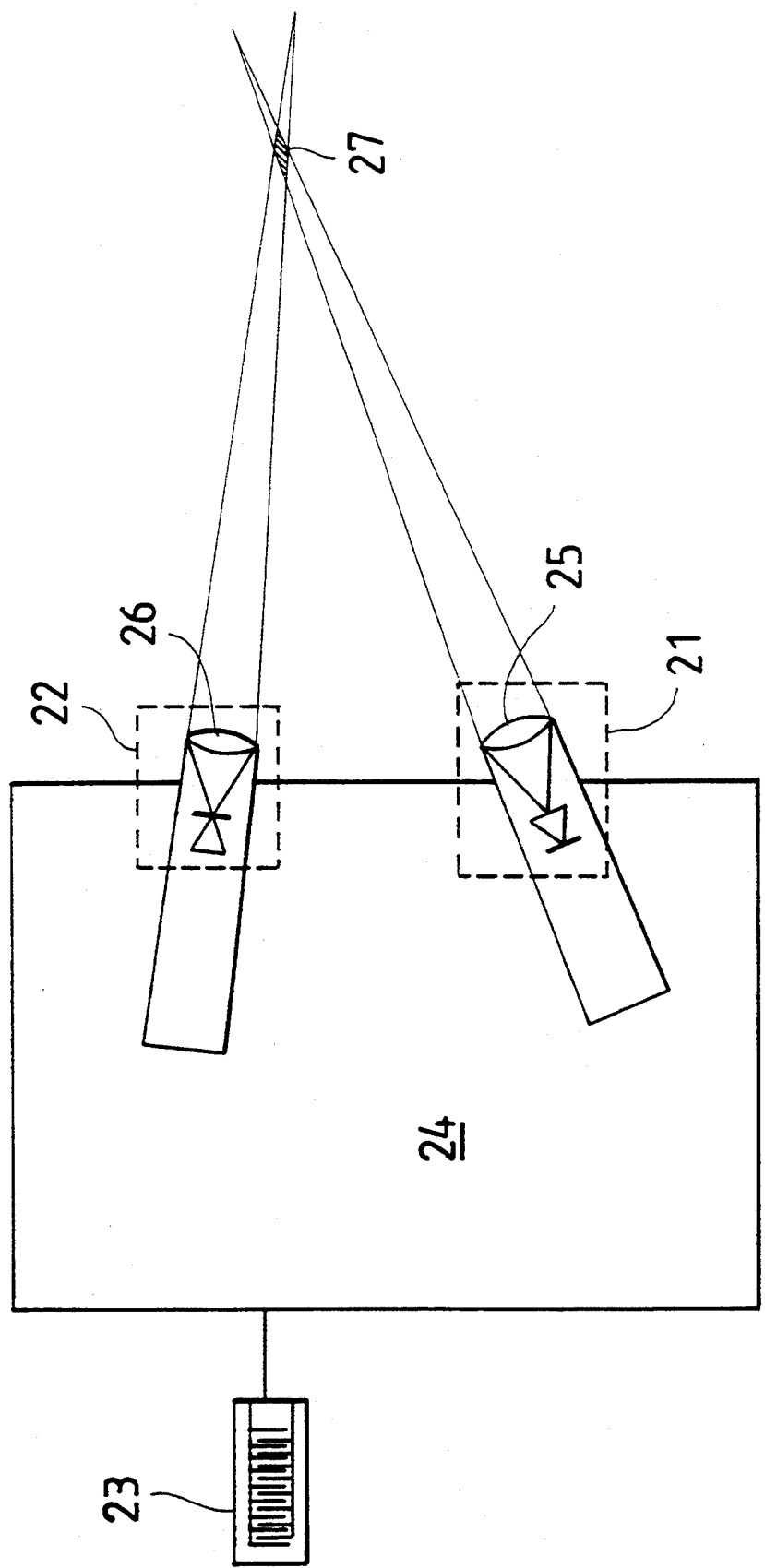
FIG. 2 shows an alternative embodiment of a measurement apparatus according to the invention for measuring prevailing weather and visibility.

FIG. 2 shows a measurement apparatus having a different measurement geometry to that illustrated in FIG. 1. The apparatus comprises all corresponding units shown in FIG. 1: a transmitter unit 22 with a lens 26, a receiver unit 21 with a lens 25, a measurement space 27 delineated by the beams of said units, a heatable capacitive sensor 23 for measurement of water volume and a computing unit 24, which takes care of measurement result processing and control of the system.

According to FIGS. 1 and 2, the apparatus is an extremely sensitive and accurate visibility meter operating in the narrow-angle forward-scatter principle. The optical precipitation analysis is based on detailed analysis of the visibility measurement signal. Real-time measurement and analysis are run with the help of an integral microcomputer of the computing unit 4.

The water-volume measurement section following the capacitive sensor 3 controls the automatic heating of the sensor's measuring surface and issues a signal for advent and cessation of precipitation as well as an analog voltage signal corresponding to the quantity of water measured on the sensor surface. The analog signal is converted into digital form and the water volume accumulated during a measurement cycle are computed from its magnitude and changes thereof.

The integral microcomputer of the computing unit 4 also performs further processing and reporting of measurement data as well as self-diagnostics of general system performance and data reliability.

A major portion of the system functions and almost all signal processing steps are implemented in the software.

Figure 4:
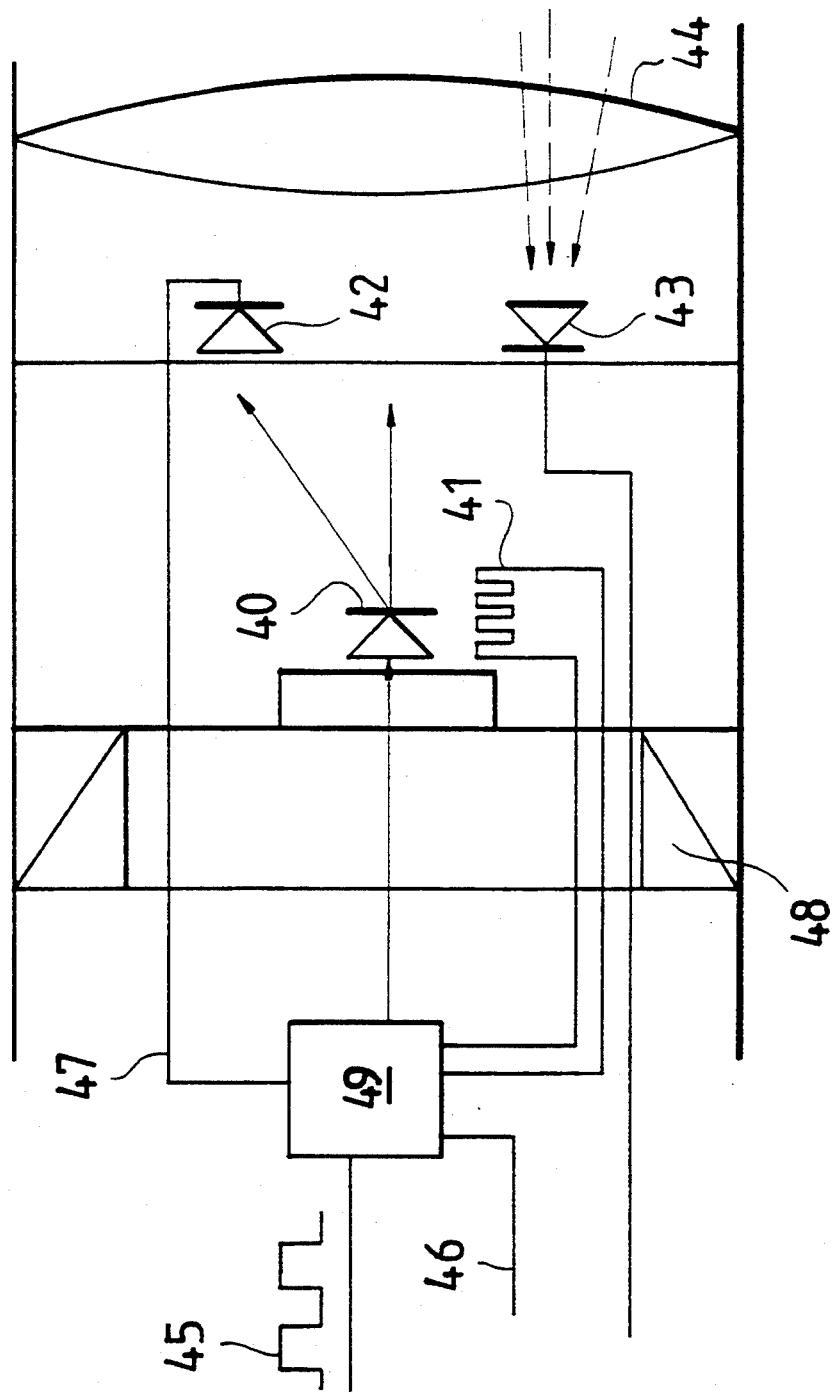
FIG. 4 shows in detail a transmitter unit according to the invention.

The measurement of the optical signals occurs according to FIGS. 4 and 3 as follows:

According to FIG. 4, an infra-red light emitting diode 40 of the transmitter unit operating at 850 nm wavelength emits light pulse-modulated at 2.3 kHz frequency. The emitted light is collimated with a lens 44 (focal length 75 mm) so that the transmitter beam is focused to a point approx. 1 m from the diode. The intensity of emitted light is stabilized by means of a controllable pulse modulator 49 against the effects of temperature drift and diode aging by virtue of a feedback circuit 47 connected to a photodiode 42 for measuring the output level of the light-emitting diode and a heater element 41 for thermostatting the operating temperature of the light-emitting diode. The pulse modulator 49 of the light-emitting diode also receives a phase-shift signal 46. Contamination of the transmitter unit lens is monitored by measuring the back-scatter of the emitted light from lens with the help of a photodiode 43. The light-emitting diode 40 is aligned by means of a mechanical centering element 48. The transmitter unit is synchronized with the receiver unit by means of a synchronizing signal 45.

Figure 3:
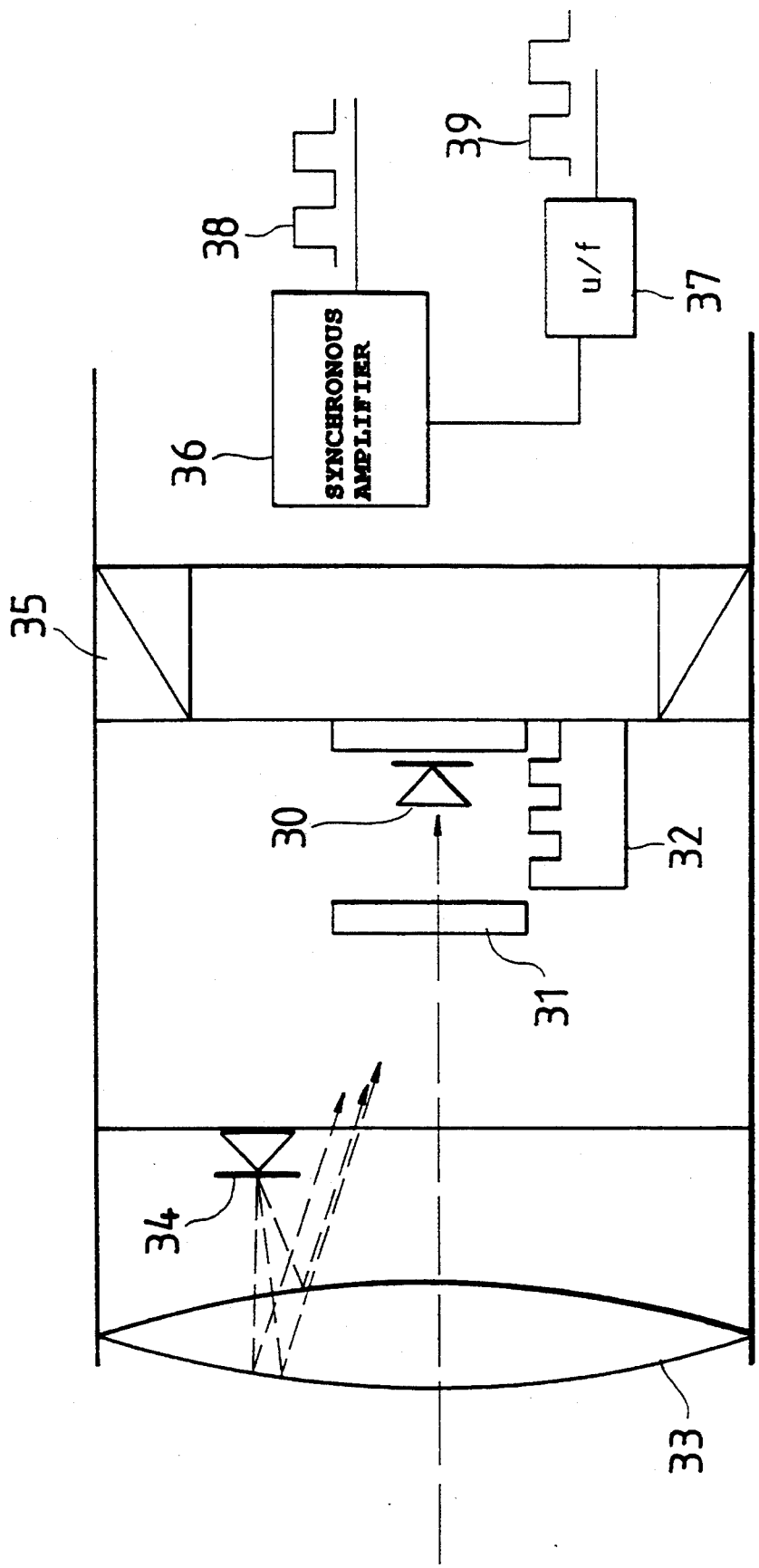
FIG. 3 shows in detail a receiver unit according to the invention.

According to FIG. 3, the receiver unit is located and aligned correspondingly so that the transmitter and receiver beams intersect making an angle of approx. 33°. Contamination of the receiver lens 33 can be monitored using a small auxiliary light-emitting diode 34, whose back-scattered light is proportional to the degree of contamination over the optical path. The PIN photodiode 30 of the receiver unit is connected to a synchronous amplifier 36 synchronized by a synchronizing signal 38. The output voltage of the amplifier is converted in a frequency (range 100 Hz . . . 10 kHz) in a voltage/frequency converter 37. The output frequency 39 of the receiver unit is measured by means of a counter circuit on the processor card of the apparatus and the processor itself. The processor receives a frequency sample signal from the counter circuit once every 4 . . . 8 ms. All frequency samples are sequentially stored in a data memory for further computing. The receiver is aligned with respect to the optical system with the help of a centering element 35. An optical filter 31 is provided for filtering away undesired wavelengths.

To measure the idling frequency and system noise, the processor controls the receiver and transmitter to operate asynchronously via, e.g., a signal line 46 shown in FIG. 4. The idling frequency thus measured is free from the contribution of scatter of the transmitted light, so it contains the idling frequency of the receiver's voltage/frequency converter and the electrical and optical noise alone.

Signal measurement and background measurement are performed alternatingly in 15 s periods, whereby the measured background ground and noise can also be considered to represent the situation prevailing during signal measurement.

The selected interval of frequency sampling corresponds to a time required for falling a distance of approx. 40 mm if the rate of fall of a particle is approx. 5 m/s which is a typical value of limiting rate of fall for a water droplet. Because the diameter of the measurement space has also been confined to approx. 40 mm by virtue of the focusing optics, the signal change caused by such a particle is detectable in a single sample on the average. Snowflakes fall slower and thus are detectable in several subsequent samples. During prevailing wind also each snowflake is detected in a single sample alone. The measurement method used for measuring the rate of fall is most inaccurate and, therefore, has not been utilized in further signal processing.

The interdigitated, glass-protected sensor surface 3 shown in FIG. 1, for example, is employed by connecting the capacitor formed by the interdigitated pattern as a part of a resonant circuit, whose resonant frequency is changed when water is allowed to land on the sensor's measuring surface. The frequency of the oscillating resonant circuit is converted into a DC signal by means of a frequency/voltage converter. A slight heating power applied to the sensor substrate keeps the measuring surface dry, thus preventing a direct condensation of humidity on the measuring surface. The heating power of the sensor surface 3 is increased when an increase in the measurement signal amplitude is detected.

Because of the extreme sensitivity of the measurement circuit to water, which is related to the exceptionally high dielectric constant of water, the detection method is not sensitive to other substances. The heated surface melts solid condensation forms of water, so the measurement method is also compatible with snow and ice.

The measurement signal converted into a DC voltage is also sampled with an analog/digital converter. The signal is sampled approximately once every second. The base signal measured from a dry surface is subtracted from these signal samples, thus permitting the water volume fallen on the measuring surface to be computed from the rapid variations of the net signal and the slowly varying part of the signal. The time constant for the averaging of the slowly varying part of the signal is appropriately adjusted to match different precipitation rates up to rainfall.

The measurement method itself is implemented as follows:

By measuring the volume of precipitation and the water volume contained in the measurement space simultaneously using the apparatus illustrated in FIG. 1 or 2, for example, the type of precipitation can be inferred from the ratio of said volumes. The apparent volume of precipitation is measured from the optical signal scatter and the quantity of contained water is obtained from the signal change caused by it in the capacitive sensor circuit. The measurement signal obtained from the optical scatter, with corrections by the precipitation information, yields the meteorological visibility reading.

The changes in the intensity of scattered light are measured using a small-volume (0.2 l) measurement space with a sampling rate of at least 20 signal samples per second. The same measurement is also performed without the light scatter signal to determine the noise level. Signal and noise measurements are performed continuously in an alternating succession.

If the sum of signal variation within a preset period remains smaller than the threshold level described above for detection of precipitation, cessation of precipitation is indicated. The detection of precipitation is duplicated by monitoring the signal level of the heated capacitive sensor's measuring surface.

When precipitation has been detected, the squares of all signal changes exceeding a preset observation threshold are computed, summed and the result is corrected by a correction factor. The final result is a figure which is proportional to apparent volume of the detected particles.

The water quantity of the precipitation is determined from the analysis of signal obtained from the measuring surface of the heated capacitive sensor. The measurement is calibrated so that during rainfall the optically measured apparent volume and the quantity of contained water are approximately equal.

The degree of freezing in precipitation is obtained from the ratio of the apparent volume of precipitation to its quantity. Precipitation is snowfall if the difference between the apparent volume and the measured water quantity is large. Precipitation is rainfall if the difference is small. Sleet forms the in-between cases.

Hailstones are detected by the condition that the singular particles are very large and that the difference between the apparent volume and the measured water quantity is large.

Drizzle is categorized as rainfall in which all measured singular particles have a size remaining below a preset limit.

The same apparatus is also used for measuring the meteorological visibility.

The visibility reading is corrected according to the precipitation reading.

Several methods are usable for measuring the water quantity. Best alternative of all would be an accurate and extremely sensitive balance. Other alternative methods are too insensitive to attain sufficient total sensitivity for the detection of precipitation type.

Coarse categorization of precipitation type is possible on the basis of temperature sensing of the measurement space.

As shown in FIG. 5, the transmitter, or alternatively, the receiver unit 50 are supportedly mounted on a lens tube 54 by means of a drilled, advantageously conically bevelled backing plate 52 and a gapped, conically bevelled ring 51. Thus, the transmitter/receiver unit 50 fixed on a base plate 56 is both centrally aligned on the optical axis determined by a lens 55 and rigidly located to the point determined by the focal length F against the lens tube 54 when bolts 53 are tightened. Here, the backing plate 52 approaching the base plate 56 pushes the conically bevelled ring 51 against the lens tube, whereby the entire system becomes solid.

What is claimed is:

1. An apparatus for determining prevailing weather and meteorological visibility, said apparatus comprising:
   optical scattering-type measurement means for generating an optical scatter signal and for determining an apparent volume of precipitation in a measurement space from the optical scatter signal;
   means for detecting a heating signal change and for determining water quantity related to the apparent volume of precipitation in the measurement space from the heating signal change, and
   data-processing means for receiving the optical scatter signal and the heating signal change, for determining a precipitation type from the measured apparent volume and the measured water quantity, and for determining the prevailing weather and meteorological visibility from the precipitation type.

2. The apparatus of claim 1, wherein said means for measuring the water quantity is a heated capacitive sensor.

3. The apparatus of claim 1, wherein said means for measuring the water quantity is a balance.

4. The apparatus of claim 1, further comprising a transmitter and/or receiver unit supported between backing plates using a gapped, conically bevelled ring.

5. A method for determining prevailing weather and meteorological visibility, comprising the steps of:
   (a) generating an optical scatter signal and determining an apparent volume of precipitation in a measurement space from the optical scatter signal;
   (b) determining a heating signal change and determining water quantity related to the apparent volume of precipitation in the measurement space from the heating signal change, and
   (c) determining a precipitation type from the measured apparent volume and the measured water quantity and determining the prevailing weather and meteorological visibility from the precipitation type.

6. The method of claim 5, wherein said step (b), the water quantity is measured by a heated capacitive sensor.

7. The method of claim 5, wherein said step (b), the water quantity is measured by a balance.

8. The method of claim 5, further comprising the step of:
   (d) measuring a size distribution of droplets or particles comprising the precipitation.

9. The method of claim 6, wherein the heated capacitive sensor is heated at a base power level continuously to keep a measuring surface of the heated capacitive sensor dry and when the measured water quantity increases above a preset limit, the base power level is increased and when the measured water quantity is below the preset limit, the base power level is decreased.

10. The method of claim 6, wherein the precipitation in solid condensation form is melted on a measuring surface of the heated capacitive sensor.

11. The method of claim 5, wherein the measured apparent volume of precipitation and the measured water quantity are calibrated to be approximately equal for rainfall.

12. The method of claim 5, wherein the apparent volume of precipitation, measured using an optical scattering-type measurement instrument and the measured water quantity are compared and if a large difference is detected, the precipitation is interpreted as snowfall.

* * * * *